United States Patent [19]
Buys et al.

[11] Patent Number: 5,336,217
[45] Date of Patent: Aug. 9, 1994

[54] PROCESS FOR TREATMENT BY IRRADIATING AN AREA OF A BODY, AND TREATMENT APPARATUS USABLE IN DERMATOLOGY FOR THE TREATMENT OF CUTANEOUS ANGIO DYSPLASIAS

[75] Inventors: Bruno Buys, Lille; Jean-Pierre Sozanski, Thumeries; Serge Mordon, Villeneuve d'Asco; Jean-Marc Brunetaud, La Madeleine; Yves Moschetto, Haubourdin, all of France

[73] Assignee: Institut National de la Sante et de la Recherche Medicale (INSEPM), Paris, France

[21] Appl. No.: 893,683

[22] Filed: Jun. 5, 1992

Related U.S. Application Data

[63] Continuation of Ser. No. 505,469, Apr. 6, 1990, abandoned, which is a continuation-in-part of Ser. No. 153,838, Dec. 30, 1987, abandoned.

[30] Foreign Application Priority Data

Apr. 24, 1986 [FR] France .................. 86 06581

[51] Int. Cl.$^5$ .............................. A61N 5/02
[52] U.S. Cl. .......................... 606/9; 606/2; 606/10; 606/12; 606/13; 607/89
[58] Field of Search ................... 606/2-19; 128/395, 397, 398; 607/88, 89

[56] References Cited

U.S. PATENT DOCUMENTS

| | | | |
|---|---|---|---|
| 4,069,823 | 11/1978 | Isakov et al. | 606/19 |
| 4,266,548 | 5/1981 | Davi | 128/303.1 |
| 4,580,557 | 4/1986 | Hertzmann | 128/303.1 |
| 4,653,495 | 3/1987 | Nanaumi | 128/303.1 |
| 4,672,969 | 6/1987 | Dew | 128/397 |
| 4,733,660 | 3/1988 | Itzkan | 606/9 |
| 4,750,486 | 6/1988 | Butler et al. | 128/303.1 |

FOREIGN PATENT DOCUMENTS

| | | | |
|---|---|---|---|
| 0130950 | 1/1985 | European Pat. Off. | A61N 5/06 |
| 0172490 | 2/1986 | European Pat. Off. | A61B 17/36 |
| 2357008 | 1/1978 | France | G06F 15/42 |

OTHER PUBLICATIONS

Laser Industries Limited Litterature on the Sharplan 771 Microscan 3 pages.

H. Fujii, T. Asakura, T. Tsuji, T. Matsumoto, & T. Ohura, "Multispot laser photocoagulation system using a fiber bundle scanner," *Applied Optics*, vol. 21, No. 19, Oct. 1, 1982, pp. 3437-3442.

H. Fujii, et al., "Fibre bundle scanner for laser photocoagulation treatment," *Optics and Laser Technology*, vol. 14, No. 1, Feb. 1982 (Buttersworth & Co. Ltd., Guildford, Great Britain), pp. 39-40.

*Primary Examiner*—David M. Shay
*Attorney, Agent, or Firm*—Limbach & Limbach

[57] ABSTRACT

The invention relates to a process of treatment in the field of dermatology, for the treatment of cutaneous angio dysplasias, using the energy emitted by a laser source, as well as to an apparatus for the treatment of skin angiomas implementing the process. The apparatus includes a laser source suitable for supplying laser radiation, a treatment instrument for receiving the laser radiation from the source and whereby a plurality of consecutive laser shots is effected to form a plurality of resulting impacts on the area of the body to be treated. Following each shot, the area of the body thus treated has, at the resulting impact, at least a given relaxation time. The apparatus includes a support frame, an optical fiber disposed in the frame. The optical fiber has two ends, the first of the ends being suitable for connection to the laser source via the connecting means, the second end being mobile and suitable for generating a displaceable laser spot. An automatic control unit with memory controls in time and space sequential scanning of the second end of the optical fiber, and permits a sequence of consecutive laser shots such that two consecutive laser shots form two resulting impacts, which are not contiguous, if the time lapse between the two consecutive laser shots is less than the given thermal relaxation time, and the impacts of the different consecutive laser shots completely cover the surface through the contiguous juxtaposition of the different impacts resulting from the different laser shots.

8 Claims, 7 Drawing Sheets

—————— PRIOR ART ——————

PROCESS FOR TREATMENT BY IRRADIATING AN AREA OF A BODY, AND TREATMENT APPARATUS USABLE IN DERMATOLOGY FOR THE TREATMENT OF CUTANEOUS ANGIO DYSPLASIAS

This is a continuation of co-pending application Ser. No. 07/505,469 filed on Apr. 6, 1990, now abandoned, which in turn was a continuation-in-part application Ser. No. 07/153,838, filed on Dec. 30, 1987, now abandoned, of Bruno Buys. et al. for PROCESS FOR TREATMENT BY IRRADIATING AN AREA OF A BODY, AND TREATMENT APPARATUS USABLE IN DERMATOLOGY FOR THE TREATMENT OF CUTANEOUS ANGIO DYSPLASIAS. It relates to a process of treatment by irradiating an area of a body, as well as to a treatment apparatus usable in dermatology for the treatment of cutaneous angio dysplasias.

BACKGROUND OF THE INVENTION

The cutaneous angio dysplasia, one example of which is the skin angioma, better known as the "port-wine stain", results from hypervascularization of the dermis which produces an unaesthetic and unsightly effect on the patient's skin.

At the present time, there are known methods of treating cutaneous angio dysplasias that consist in blocking the blood vessels in the skin area concerned so as to obtain permanent discoloration of the lesion without thereby producing any side effects.

Nowadays, the laser technique is generally used by the practitioner to block the blood vessels manually by photocoagulation with the help of a laser, for example, an Argon-type laser.

In particular, an Argon laser produces radiation that is suitable for the treatment of cutaneous anglo dysplasias as it is well absorbed by the living tissues with a preferential effect on the red and black pigments. That is why the thermal effects of the Argon laser are often used in the treatment of such symptoms.

With specific regard to the treatment of cutaneous angio dysplasias, the desired thermal effects correspond to a temperature of between 60° and 80° C., which has to be confined to the micro-vessels of the dermis to avoid any necrosis of the tissues presenting risks of scar formation.

In general, this method of treatment is carried out manually by the practitioner who, using an Argon laser source equipped with a controlled attenuating shutter for adjusting the irradiation time and an optical fiber to transmit the laser energy generating a laser spot, effects laser shots to produce a plurality of closely grouped impacts on the area to be treated.

In this case, the practitioner's skill is of prime importance as he has to exercise control over all the treatment parameters, namely radiation power, exposure time, the relative positioning of the different impacts and their uniformity.

The success of the treatment thus depends primarily on the practitioner and his skill in controlling these parameters which can determine a wide range of thermal effects, both in terms of the temperature attained which leads either to coagulation or to volatilization, and of the localization of this temperature rise.

Owing to these different parameters that have to be taken into consideration, the present efficiency of such a treatment corresponds to about 50 to 60% of successful results and patients are thus compelled to apply to highly experienced practitioners as success depends essentially thereon.

Moreover, in most cases, cutaneous anglo dysplasias cover large areas, in the order of several square centimeters, which are not always flat surfaces and, as the diameter of the elementary laser spots at the impacts is in the order of one millimeter, the practitioner, when applying the treatment, will be compelled to juxtapose several hundreds of shots manually with practically no positioning references.

Indeed, owing to the technique used, the practitioner is obliged to wear protective goggles and he does not, therefore, have a clear view of the spot that he is positioning. This also makes it difficult to keep the diameter of the spots produced uniform as this depends essentially on the distance between the optical fiber and the area under investigation.

Furthermore, when these methods are used, local anaesthesia is systematically practised to prevent the patient from experiencing the pain inherent in accumulations of heat.

The cumulative effect of these requirements makes this method of treatment difficult and tedious to apply; moreover, the treatment has to be spread out over several sessions, on one hand for the sake of the patient, who has to keep still during treatment, and, on the other hand, for the practitioner, who has to make an effort of sustained concentration.

To minimize the proportion of failures encountered with this treatment and to facilitate the practitioner's work, the use of robotics has already been contemplated to automate the task.

A few years ago, in fact, treatment equipment was presented that was essentially composed of a robot arm ensuring the controlled movement of a hand-piece in which the optical fiber was disposed.

This method has not been further developed to date as its implementation is a delicate matter since it presupposes the detection of three-dimensional shapes and does not make any allowances for the patient's movements during treatment.

While this equipment facilitates the practitioner's work, it gives results that are inferior to those obtained using the traditional manual method.

On the other hand, it is also known to use a hand tool, designed according to the same principle as the above-mentioned device, that is positioned by the practitioner, that is to say with the help of an optical fiber contained in a portable case transmitting the energy of a laser source, but the elementary spot of which has been spread by using an anamorphic optical system.

However, with this instrument, it is difficult to make the spot uniform and, in addition, the depth of field is very small. Furthermore, to observe the treatment parameters mentioned earlier, use is made of a high-power laser source, which is an obstacle to its development as this increases the cost of such a system.

There is also known, in particular from U.S. Pat. No. 4,653,495 an apparatus for treating skin angiomas using the energy emitted by a laser source, as shown in FIG. 1.

This apparatus comprises a laser source 61, suitable for emitting a laser beam 62, which is then directed towards an optical system 64 suitable for positioning the laser beam in front of a plurality of optical fibers grouped together at a laser beam scanning unit 63.

More precisely, laser beam 62 is directed towards a mirror 66 and then focussed by a lens 67, and subsequently transmitted to a horizontal layer of optical fibers 69.

As shown in the figure, the apparatus comprises 17 optical fibers, numbered from 69-1 to 69-17.

One of the optical fibers, 69-1, is suitable for transmitting the laser energy to a "single" hand-piece numbered 70. The other 16 optical fibers, 69-2 to 69-17, form a torus and can be directed to a second "multi" hand-piece numbered 71.

During the treatment, the operator can choose to use either the "single" hand-piece 70 or the "multi" hand-piece 71, depending on the size and shape of the area to be treated.

If he decides to use "single" hand-piece 70, the practitioner will then operate manually in accordance with the method of treatment described earlier. It should be noted that this hand-piece can also be used to measure irradiation power by inserting the end of "single" hand-piece 70 into a power measuring device 72.

If the practitioner does not wish to scan the area for treatment manually using "single" hand-piece 70, he can then choose to use the other "multi" hand-piece 71, which will enable him to treat a larger surface area.

In this connection, as shown, in particular, in FIGS. 2a to 2c, there is known a method of treatment referred to as the "zebrine pattern". Up to the time of the present invention, this method was considered as one of the best as it permitted faster treatment than the manual process.

The "zebrine pattern" technique consists in producing a succession of parallel lines of laser impacts 85 having a diameter "d" and spaced apart by a center to center distance "e".

FIG. 2a shows such lines of impacts numbered 80 and 81 which induce the coagulation of two corresponding strips, 80' and 81' on the area to be treated, as shown in FIG. 2b.

After this treatment, hand-piece 21 is re-positioned and two new lines, 82 and 83, of impacts 85 having a diameter "d", and equally spaced apart by a center to center distance of "e", are produced.

As shown in FIG. 2c, these two new lines, 82,83, induce fresh treated strips 82' and 83', which determines a treated surface 80'-83'.

To make it possible to proceed in this way, the end face 71a of "multi" hand-piece 71 has an arrangement of optical fibers 69-2 to 69-17 such as to form impact lines that are parallel and spaced in relation to one another so as to observe the "zebrine pattern" method.

This being so, in certain cases in which the area for treatment is smaller than working surface 71a, this end 71a will advantageously be provided with a mask 73 and a protective end piece 74.

Such a device makes for genuine progress in relation to the manual method of treatment, but it does have numerous drawbacks inherent, on one hand, in the very design of the apparatus and, on the other hand, in the difficulty of repositioning the "multi" hand-piece, as well as in the substantial contamination of the end of the latter.

As regards the structure of such a known device, it is essential, in the first place, to use a bundle of optical fibers arranged in a torus in accordance with a particular type of cabling, namely by causing the fibers of a layer forming cabling configuration to come to form a toroidal cabling configuration, which has an effect on the dimensioning of "multi" hand-piece 71 and on the flexibility of the system as a whole.

Furthermore, at input 63 to the bundle of optical fibers 69, it is necessary to scan the layer of fibers with the laser beam by positioning the latter opposite each end of the optical fibers and on their longitudinal axis via the device 64,66,67. Major problems arise in connection with the design of such a mechanical positioning device, which has to hair precisely and successively opposite each fibre disposed in the layer. This non-material positioning of the laser beam along the axis of the fibers is an extremely delicate matter.

As to the application of the treatment, it should be noted that considerable difficulties are involved in repositioning the end 71a of the "multi" hand-piece 71 in order to intercalate new lines 82,83 of impacts between the already treated strips 80' and 81', as shown in particular in FIG. 2b.

This method of working is rendered necessary by the effect of thermal diffusion around the impacts made which causes heat accumulation that has to be taken into account in order to avoid overheating in the area treated.

Similarly, to allow for the Gaussian profile of the laser spot emitted, it is necessary, in certain case, to create overlapping impacts, as also shown in FIG. 2.

Moreover, in order to increase the surface area treated, we have to turn to large diameter fibers. There are thus devised, in U.S. Pat. No. 4,653,495, laser fibres of a polygonal cross-section to permit better coverage of the surface treated; however, these are technically impossible to produce by means of flexible optical fiber manufacturing processes known to date.

This being the case, it is to be noted that the apparatus described in this U.S. patent works in contact with the skin, that is to say the end 71a of "multi" hand-piece 71 has to be placed in direct contact with the area to be treated.

Such a procedure increases the difficulty of repositioning the hand-piece at a subsequent stage and, moreover, leads to contamination of the ends of the optical fibers.

As a result of all these major drawbacks, no apparatus according to U.S. Pat. No. 4,653,495 is yet on the market or in service in medical circles.

This being the case, in a completely different medical field, DAVI, U.S. Pat. No. 4,266,548 discloses a process and a device, using laser energy, for excising pathological tissues. This process consists in vaporizing pathological tissues inside a patient's body.

Such an apparatus is composed of a laser source, a collimator, a flexible optical waveguide linking the laser source to the collimator, a device for deflecting the laser beam inside the collimator, as well as a mechanical device for prepositioning the collimator assembly outside a patient at X, Y, Z.

To operate inside a patient, the collimator ends in a rigid cannula which forms a waveguide and which enables the laser energy to be directed towards the tissue to be vaporized.

To give the laser beam a certain radius of activity within the patient's body, the deflector device, comprising in particular a deflector crystal, subjected to mechanical stresses via electrodes, makes it possible to deflect the laser beam within a range of small amplitude.

In such a case, it is to be noted that we are concerned with an invasive surgical operation to introduce the cannula into the patient's body and it is therefore necessary to preposition the collimator at X,Y,Z outside the patient.

This prepositioning is carried out using a traditional mechanical assembly composed of three motors equipped with endless screws placed on the three axes X,Y,Z, the dimensions of which are very large.

The problem posed by this document, U.S. Pat. No. 4,266,548, is completely different from those inherent in the treatment of skin angiomas and it is in no case possible to transpose this technique to the invention.

SUMMARY OF THE INVENTION

The object of the present invention is to provide a process of treatment by irradiation of an area of a body, as well as an apparatus for treatment usable in dermatology for treating cutaneous angio dysplasias that make it possible to take over the functions dependent on the skill of the practitioner by controlling each of the parameters required for the treatment and which, furthermore, make it possible to overcome the drawbacks of those systematized apparatus that have been devised to date and which have not found applications.

The inventors' first task was to analyze and study precisely the different parameters governing the treatment of cutaneous angio dysplasias based on the energy emitted by a laser source.

As pointed out earlier, good results are obtained by treating angiomas using an Argon laser which permits thermal coagulation and enables the blood vessels thus treated to be blocked. However, the irradiation of these areas necessitates precise control as any rise in temperature above the desired temperature leads to irreversible damage and the risk of scar formation.

One of the parameters to be monitored resides in the effect of thermal diffusion around the impact made which causes an accumulation of heat that will have to be controlled. This parameter is linked to the fluence supplied to the tissue treated, which is defined by the following relation:

$$\frac{\text{Power of laser radiation emitted} \times \text{exposure time}}{\text{Surface of spot}}$$

In this connection, the inventors have analyzed these effects, which are illustrated in annexed FIGS. 3 to 5.

FIG. 3 provides a three-dimensional representation of a thermal image, obtained with an infrared camera, on the patient's skin following a laser shot. FIG. 4 shows the variations in temperature, at the cross-section along axis IV—IV of FIG. 3, as a function of distance from the laser shot impact. Finally, FIG. 5 represents the variations in temperature of a point A of FIG. 4 of the impact resulting from the said laser shot, after the said firing, as a time function. Specifically, when a laser shot is fired at the body to be treated, the temperature is raised punctually, but the inventors have also observed a phenomenon of geographical diffusion all around the impact, as represented in the three-dimensional graph in FIG. 3.

Furthermore, this temperature rise, due to the laser shot, occurs very swiftly; a temperature peak is obtained, for example, within the space of approximately 400 milliseconds.

In this connection, temperature diffusion at skin level is illustrated in FIG. 4, which shows such a temperature rise over a diameter in the order of 3 to 4 millimeters with, of course, a temperature maximum on the axis of the laser shot and the resulting impact.

Cooling then takes place slowly, as shown, in particular, in FIG. 5, and the thermal relaxation time is in the order of 1.5 seconds after firing, this being for temperature diffusion confined to a diameter, about the axis of firing, of 3 to 4 millimeters at skin level. In other words, in this diameter, after a period of 1.5 seconds has elapsed, it is considered that the initial temperature of the body has been restored.

One of the aims of the present invention has been to take account of this study concerning the phenomenon of geographical distribution all around the impact, and to optimize the treatment process by carrying out a series of consecutive laser shots such as to make it possible to avoid the phenomena of heat accumulation and heat overdosage at skin level. Such optimization leads to a treatment that is easier to implement and, above all, to a treatment that is faster, thus enabling the treatment time to be reduced.

Another of the aims of the present invention is to provide a process and a systematized treatment instrument that make it possible to achieve a substantial increase in the percentage of successes obtained in the treatment of cutaneous anglo dysplasias by comparison with currently known methods.

A further object of the present invention is to provide a process and a systematized treatment apparatus permitting the treatment of cutaneous anglo dysplasias on the basis of perfectly known, reproducible geometrical areas and which, for a single positioning of the instrument, permit the ideal, efficient treatment of surface areas of up to 2.6 cm$^2$, whereas the optical fiber used generally only permits an elementary spot of approximately 1 mm in diameter.

Another object of the present invention is to provide a process and a systematized treatment apparatus, particularly usable in dermatology for the treatment of skin angiomas which make it possible to control the thermal parameters by monitoring irradiation power, the instrument-to-impact distance, exposure time and, at the same time, to control the geometrical parameters, namely the uniformity of the elementary spots and their precise, contiguous juxtaposition.

A further object of the invention is to provide a process and a systematized treatment apparatus that make it possible to allow for the thermal relaxation time associated with the diffusion of heat at the impact and, consequently, to avoid any heat overdosage.

Thus, it will be possible to dispense with the said local anaesthesia currently applied systematically to the area under treatment when using the known techniques.

Yet another object of the present invention is to provide a process and a systematized treatment instrument, usable particularly in dermatology for the treatment of angiomas which, by means of a programmed sequential scanning mode, permit consecutive laser shots such that two resulting impacts formed are not contiguous on either on the abscissa or on the ordinate if the time lapse between the said two consecutive laser shots is less than the said thermal relaxation time, and which nonetheless make it possible, when the firing sequence is completed, to cover the surface treated with juxtaposed, contiguous impacts, in other words covering the entire area treated under investigation by the treatment instrument.

This represents substantial progress by comparison with the manual method or with the systematized process devised, such as that of NANAUMI, described in U.S. Pat. No. 4,653,495. This progress is inherent in the process developed by the inventors, as in the structure of the apparatus developed, which did not exist hitherto.

One of the objectives of the present invention is to design a treatment apparatus using a laser source and a hand-piece that is small in size, easy for the practitioner to handle, organized around a single optical fiber but nonetheless permitting the treatment of a surface as large as 2 to 3 cm$^2$, this being effected in a cycle time of less than one minute.

Another object of the present invention is to provide a process and a treatment apparatus intended for the treatment of cutaneous angio dysplasias that permit the treatment, with a single positioning, of an elementary geometrical surface, working at a distance from the skin, which, on one hand, enables the practitioner to view the area undergoing treatment and, on the other hand, avoids contamination of the fibers that arises when equipment is used in contact with the skin. Furthermore, this structure makes it very easy for the practitioner to reposition the hand-piece in relation to an area already treated.

This remedies the drawbacks of the above-mentioned devices operating according to the "zebrine pattern" technique or operating according to a checker pattern. It should be noted that such precise repositioning in this case is practically impossible.

According to the present invention, the treatment apparatus, and, more specifically, the hand-piece, makes it possible to project the image of the end of the radiating fiber onto the skin from a distance, without any physical contact, and without contamination. Operations are carried out by optical imaging; it is virtually as if one were working against the skin. However, this is not the case, hence no contamination occurs, which is another very important advantage of the present invention over the state of the art.

Other objects and advantages of the present invention will emerge from the following description which is only given, however, by way of non-limitative illustration.

According to the present invention, there is provided a process for the treatment by irradiation of an area of a body, intended in dermatology for the treatment of cutaneous angio dysplasias, using the energy emitted by a laser source, whereby photocoagulation of blood vessels is carried out by punctual heating engendered by laser shot impacts, following each shot, the area of the body thus treated, at the said resulting impact, having a given relaxation time, as well as a given area with a diameter of diffusion of the temperature around the impact, the process comprising at least the following steps:

the energy emitted by the laser source is transported in an optical fiber having two ends, the first being fixed and receiving the laser energy, the second being mobile to provide a "displaceable" laser spot, an elementary treatment surface is defined, the positioning of the second mobile end of the optical fiber is controlled, on the abscissa and on the ordinate, in a plane that is substantially parallel to the elementary surface, a sequence of consecutive laser shots is produced, and the elementary surface is scanned from the "displaceable" laser spot in order to distribute a plurality of laser shots and, consequently, to produce a plurality of resulting impacts at the elementary surface, the sequence of laser shots is controlled in such a way that at least:

first, when two consecutive shots are fired, the resulting two impacts formed are not contiguous, either on the abscissa or on the ordinate, if the time lapse between the said two consecutive laser shots is less than the given thermal relaxation time, and second, when the firing sequence is over, the entire elementary surface has been covered by the impacts, the latter being juxtaposed and contiguous.

According to the invention, the apparatus for treating an area of a body usable in dermatology for the treatment of skin angiomas includes:

A) a laser source suitable for supplying laser radiation,

B) a treatment instrument, known as a "hand-piece", suitable for receiving the laser radiation from the source and whereby a plurality of consecutive laser shots is effected to form a plurality of resulting impacts on the area of the body to be treated, following each shot, the area of the body thus treated having, at the resulting impact, at least a given relaxation time, the hand-piece comprising:

a) a support frame, b) means for connecting the hand-piece to the laser source, c) an optical fiber disposed in the frame, having two ends, the first of the ends being suitable for connection to the laser source via the connecting means, the second end being mobile and suitable for generating a displaceable laser spot, d) imaging means, including at least one imaging lens system, disposed under the end of the optical fiber, meking it possible, from the elementary spot to form, upon effecting a laser shot, a resulting impact in the area to be treated, e) means for positioning the unit formed, on one hand, by the end of the optical fiber and, on the other hand, by the imaging means, suitable for positioning the unit thus formed in relation to the area to be treated in order to establish the firing distance, the size and the uniformity of the impacts, as well as to define an elementary treatment surface, f) sequential scanning means for displacing the second end of the optical fiber, along the referenced abscissa and ordinate, over the entire elementary surface, g) shutter means controlled and synchronized with the scanning means for controlling each shot from the displaceable laser spot, h) automatic control means with memory for controlling in time and space the sequential scanning of the second end of the optical fiber, the means permitting a sequence of consecutive laser shots such that:

first, two consecutive laser shots form two resulting impacts, which are not contiguous, either on the abscissa or on the ordinate, if the time lapse between the said two consecutive laser shots is less than the given thermal relaxation time, and second, the impacts of the different consecutive laser shots completely cover the elementary surface through the contiguous juxtaposition of the different impacts resulting from the different laser shots, this being the case at the end of the sequence.

DESCRIPTION OF A PREFERRED FORM OF EMBODIMENT OF THE INVENTION

Figure 1:
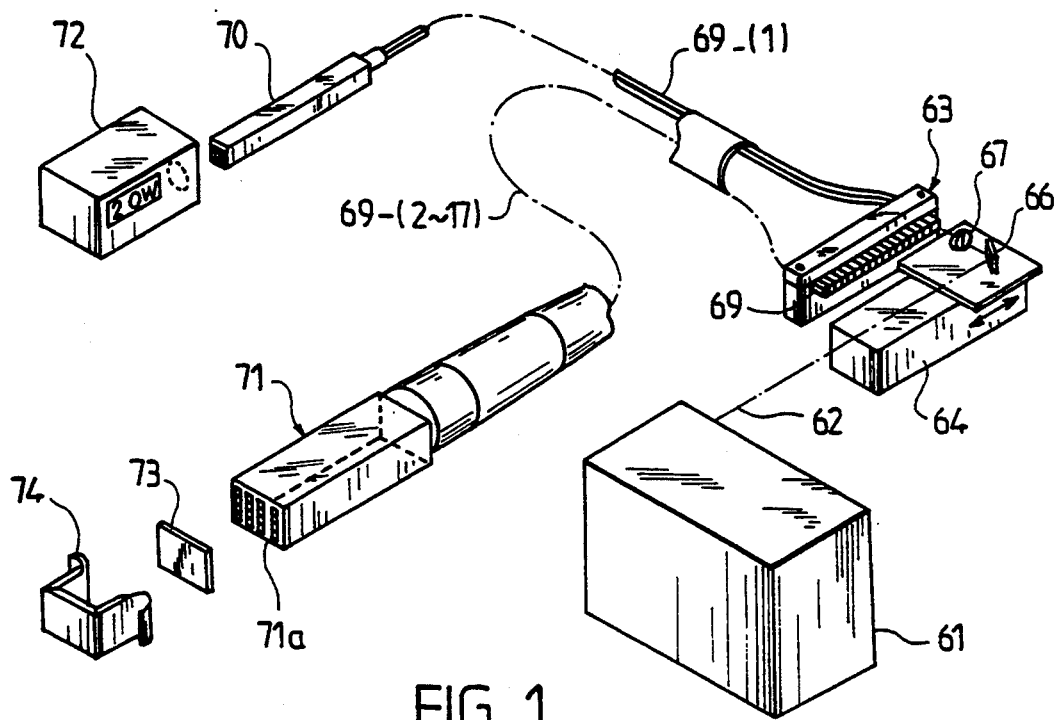
FIG. 1 shows the design of a prior art dermatology treatment apparatus usable for the treatment of skin angiomas.

The invention relates to a process of treatment by irradiation of an area of a body, intended, in dermatology, for the treatment of cutaneous angio dysplasias, as well as to a treatment apparatus permitting the implementation of the process.

However, it should be noted that the apparatus could be used for any other application involving the treatment of an area of the body necessitating these effects. In addition, the term "body" should be taken in its broadest sense, that is to say that it can be formed by living tissues or by any other, inert, matter. Furthermore, the expression "area under investigation", identified by reference number 2 in FIGS. 6, 7, 11 and 12, is to be taken as meaning the elementary surface that is exposed to the effects of the systematized treatment instrument of the invention when it is positioned on the body to be treated.

The systematized treatment apparatus of the present invention includes, generally speaking, means for treating an area of a body that will use the thermal effects of a laser source in order to obtain, in the case of skin angiomas, the blocking of the blood vessels of the dermis by photocoagulation.

To implement such a treatment process reliably, and to optimize the result obtained, it is essential to have complete control over a number of basic parameters, thermal parameters on one hand and geometrical parameters on the other hand.

It should, in fact, be borne in mind that, to control the treatment process, it is necessary to control irradiation power, exposure time, and consequently fluence, and to make allowances for the effect of thermal diffusion in order to avoid any temperature overload at the impacts. In the case of skin angiomas, these various thermal parameters should lead to accurate imagery on the vessel to be coagulated and the heating temperature should be between 60° and 80° C. to avoid any risk of undesirable scar formation.

As regards the geometrical parameters, the object is to control the uniformity of the impacts produced and their accurate juxtaposition in order for the area under investigation or elementary treatment area to be completely covered by a plurality of juxtaposed impacts caused by consecutive laser shots.

Moreover, it is necessary to define the size of this area under investigation, according to the particular case involved, in order to allow, on one hand, for the geometry of the area under investigation and, on the other hand, to spare the patient any discomfort during the treatment.

In the case of skin angiomas, which generally take up a large area, in the order of several square centimeters, the maximum size of elementary surface 2 to be treated will thus be restricted voluntarily.

A cutaneous anglo dysplasia can, in fact, have highly irregular and varied surface features in the three dimensions as, for example, in the case of a cheek or the wing of the nose. The size of elementary surface 2 will thus be limited so that the surface treated can be considered as flat in order to maintain a constant firing distance. This will also make it possible to reduce the time for which the patient has to keep still to within reasonable limits, of less than one minute.

Figure 7:
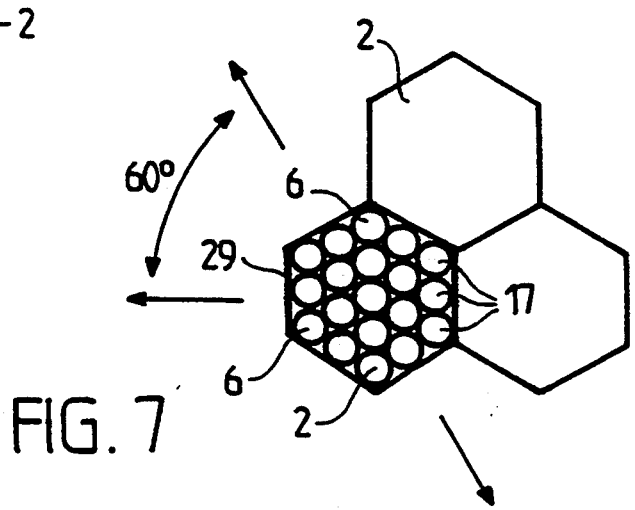
FIG. 7 shows a preferred arrangement of the elementary treatment surfaces formed by the juxtaposition of impacts according to the present invention.

To cover the totality of the lesion, the practitioner, instead of performing manual juxtaposition using the traditional method, or interlacing the areas treated with a systematized device functioning in accordance with the "zebrine pattern" method, will simply have to juxtapose manually the elementary surfaces 2, as shown, in particular, in FIG. 7. This will make it possible to reduce the number of positioning operations very considerably, facilitate positioning and substantially cut down treatment time.

According to the present invention, the process and the systematized treatment apparatus thus make it possible to meet the aforementioned objectives and to automate the treatment in a reliable, controlled manner within the elementary surface area exposed to the action of the treatment instrument.

The present invention will be more readily understood from the following description provided in connection with FIGS. 6 to 14 which supply an illustration of the principle as well as of a preferred form of embodiment of the invention.

Figure 14:
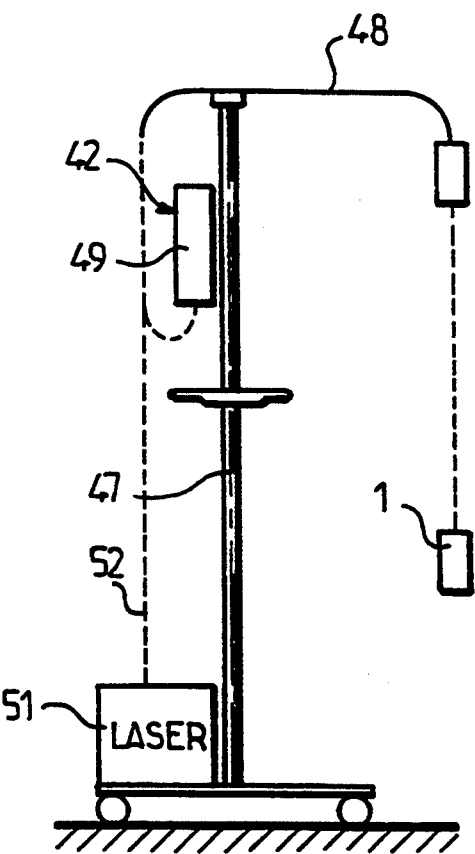
FIG. 14 shows the possible installation of the treatment apparatus according to the present invention on a bracket to facilitate its use by the practitioner.

The apparatus, according to the present invention, for treating an area of a body comprises, on one hand, a laser source, suitable for supplying laser radiation, as schematically represented at 51 in FIG. 14, and, on the other hand, a treatment instrument 1, termed a "handpiece", illustrated in detailed FIGS. 6, 8, 9 and 10, suitable for receiving the laser radiation from the laser source, and by which a plurality of consecutive laser shots are made to form a plurality of resulting impacts in the area of the body to be treated.

The laser source is, in particular, constituted by an Argon laser, known to one skilled in the art, the emission of which is continuous and regulated, in general, in multi-rays of 487 to 514 nm.

As also shown in FIG. 14, the laser source is connected to the hand-piece 1 by a flexible element 52, constituted according to known techniques and using, in particular, optical fiber technology to convey the laser energy.

For example, this flexible element providing optical interconnections between the laser source and the hand-piece is composed of an optical connector compatible with the laser source, an optical fiber guided through a first sheath of PTFE and then mechanically protected by a stainless steel spiral sheath.

It should be noted that this flexible element will also provide the electrical interconnections between the control box, schematically represented at 42 in FIG. 14, and hand-piece 1. Thus, the bundle of electric cables from control box 42 will join up a certain way along the spiral sheath via a metallic Y junction.

The fiber, PTFE sheath and coaxial bundle assembly is, in turn, protected by a larger diameter stainless steel spiral sheath determined by a connection 4,7, designed to couple the flexible assembly and the hand-piece.

Such an arrangement makes it possible, on one hand, to mechanically suspend the hand-piece while retaining a certain degree of flexibility. For this reason, the electric cables are coaxially arranged in a double twist to give maximum flexibility. In addition, the Teflon or PTFE sheath permits complete interchangeability of the fiber of connecting flexible element 52.

As to the treatment instrument or hand-piece 1, it is constructed around a support frame 3, composed of an equipment support plate 53 and a bracket 20, serving to support the different components.

Note specifically, in the support frame 3 is disposed an optical fiber 5 permitting the transmission of laser energy. This optical fiber has two ends, the first, 90, being suitable for connection to the laser source via connecting means 4, while the second end, 9, is mobile and capable of generating a displaceable laser spot 6, at the impact with the area under investigation 2.

Figure 8:
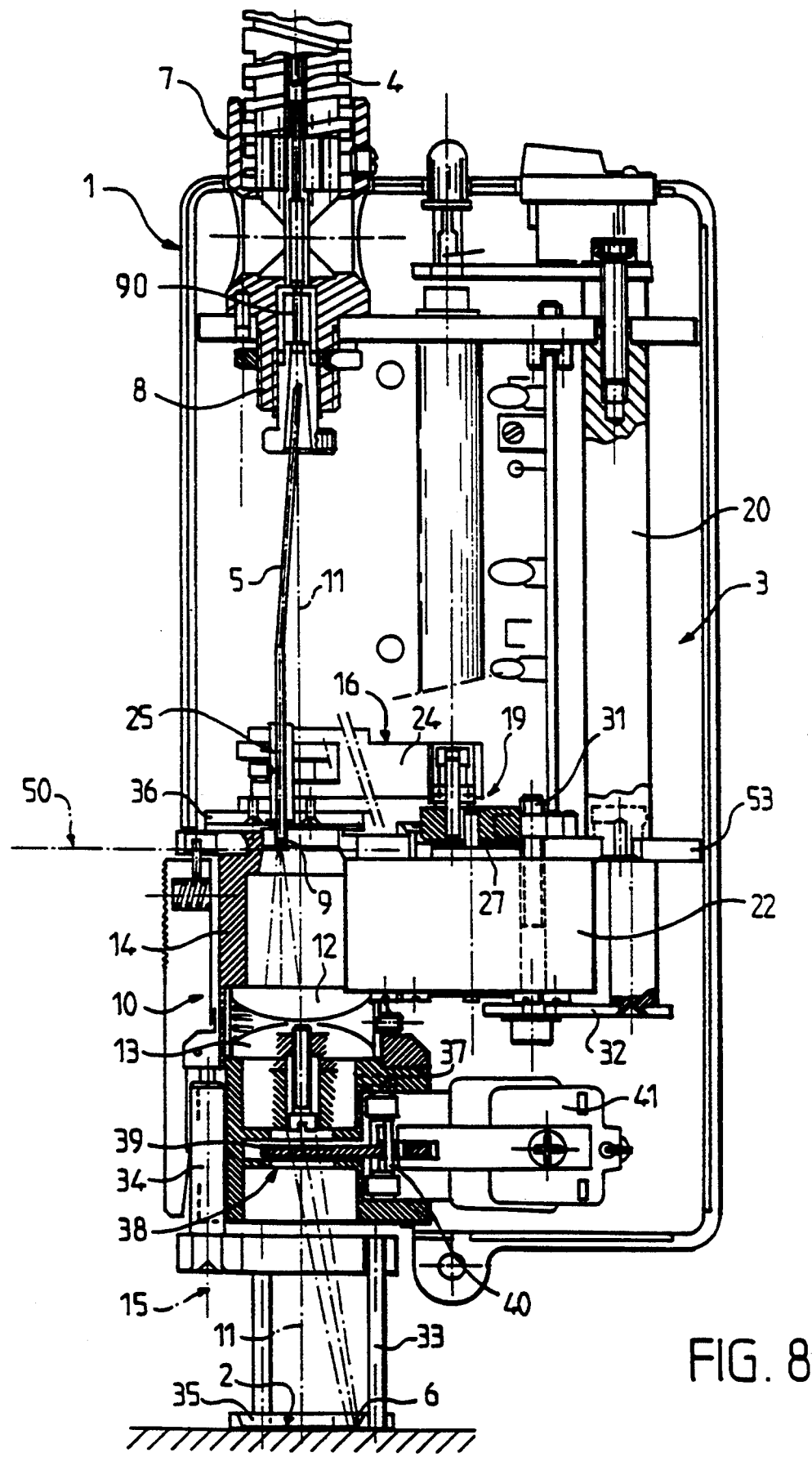
FIG. 8 shows a cross-sectional view of a preferred form of embodiment of the treatment instrument designed according to the present invention.

As to means 4 for connecting the hand-piece to the laser source, generally identified by reference number 4 in FIG. 8, these are advantageously constituted by a connector, known to one skilled in the art, which includes a centering and immobilizing system 8, of the stuffing box type, immobilizing the end 54 of the fiber.

Optical fiber 5 is, in fact, advantageously at least immobilized at a fixed point 7 of the frame 3, which thus bears these said connecting means 4. Furthermore, use will advantageously be made of an optical fiber the diameter of which will ultimately make it possible to obtain a displaceable spot 6 and a resulting impact having a diameter of between 0.5 and 2 mm. Good results have been obtained using a fiber the core diameter of which is on the order of 400 microns.

Furthermore, the end 9 of optical fiber 5, mounted on frame 3, provides a mobile laser radiation source of low inertia to generate a displaceable laser spot 6.

For this purpose, the end 9 of the optical fiber is placed opposite imaging means 10, the assembly formed by optical fibers 5 and imaging means 10 then defining an optical main axis 11.

As to the design of the imaging means 10, properly speaking, they include at least an imaging lens system 10 constituted by two plano-convex lenses 12,13 forming a symmetrical doublet, according to conventional techniques, centered on main axis 11. This doublet is axially immobilized and integral with frame 3 via mounting 14.

It should be noted that, as a result of this arrangement, the inverted image of end 9 of the optical fiber and its movements is re-formed. In addition, its aperture will be such that the beam emerging from the optical fiber is intercepted to cover the entire elementary surface 2 to be treated.

Moreover, according to the present invention, the hand-piece 1 comprises, on one hand, means 15 for positioning the assembly formed, on one hand, by end 9 of optical fiber 5 and, on the other hand, by the imaging means 10, suitable for positioning the assembly thus formed relatively in respect of the area for treatment 2 to establish the firing distance, the size and the uniformity of the impacts, as well as to define the elementary treatment surface 2 and, on the other hand, sequential scanning means 16 for displacing the second end 9 of the optical fiber, along referenced abscissa and ordinate, over the entire elementary surface.

These scanning means make it possible to implement the process of the present invention whereby blood vessels undergo photocoagulation by punctual heating generated by laser shot impacts.

Figure 3:
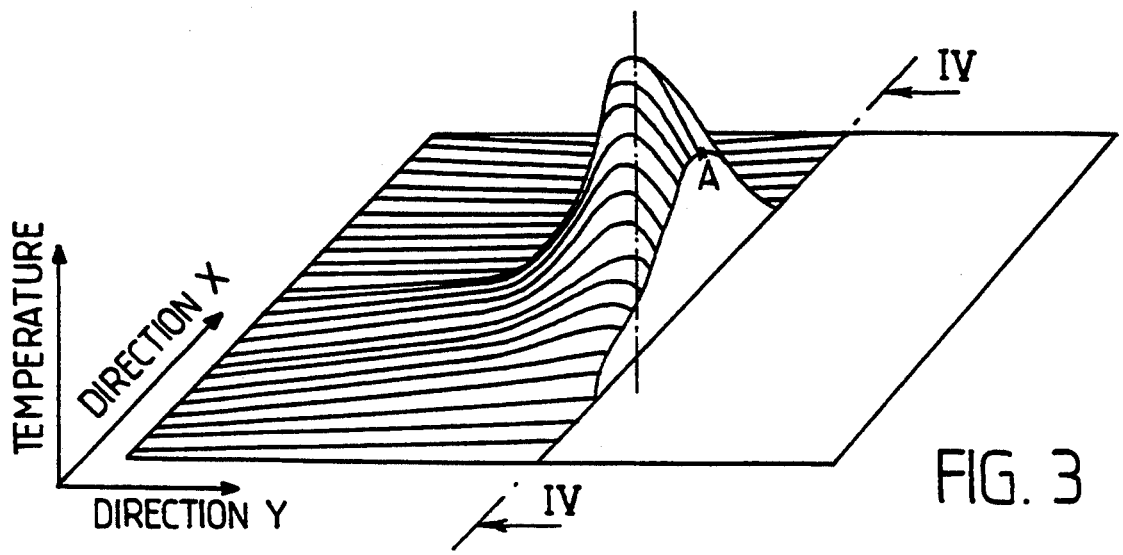
FIG. 3 schematically represents the study carried out by the inventors and shows three dimensionally a thermal image on a patient's body following a laser shot.

In this connection, following each shot, the area of the body thus treated, at the resulting impact, has a given thermal relaxation time, as well as a given area having a diameter of temperature diffusion around the impact, as explained earlier with reference to FIGS. 3, 4, 5.

Similarly, as mentioned previously, the energy emitted by the laser source is conveyed through an optical fiber having two ends, one of them secured to the source, while the other is mobile and supplies the displaceable laser spot.

This being the case, an elementary treatment surface 2 is defined and the positioning of the second, mobile, end 9 of the optical fiber 5 is controlled, on the abscissa and ordinate, in a plane that is substantially parallel, identified by reference number 50 in FIG. 8, to the elementary surface 2.

Then, to carry out the treatment, a sequence of consecutive laser shots is formed, and the elementary surface 2 is scanned from the displaceable laser spot 6 in order to distribute a plurality of laser shots and, in consequence, to produce a plurality of resulting impacts 17 on the elementary surface 2.

For this purpose, the sequence of laser shots is regulated in such a way that at least:

first, upon two consecutive shots, the resulting two impacts 17 formed are not contiguous, either on the abscissa or on the ordinate, if the time lapse between the two consecutive laser shots is less than the given thermal relaxation time, second, when the sequence of shots is over, the entire elementary surface 2 has been covered by the impacts 17, the latter being juxtaposed and contiguous, as shown in FIG. 7.

It is this control of the sequence of shots that is optimized according to the present invention in order to avoid the effects of thermal accumulation due to the temperature diffusion on the periphery of an impact.

Figure 5:
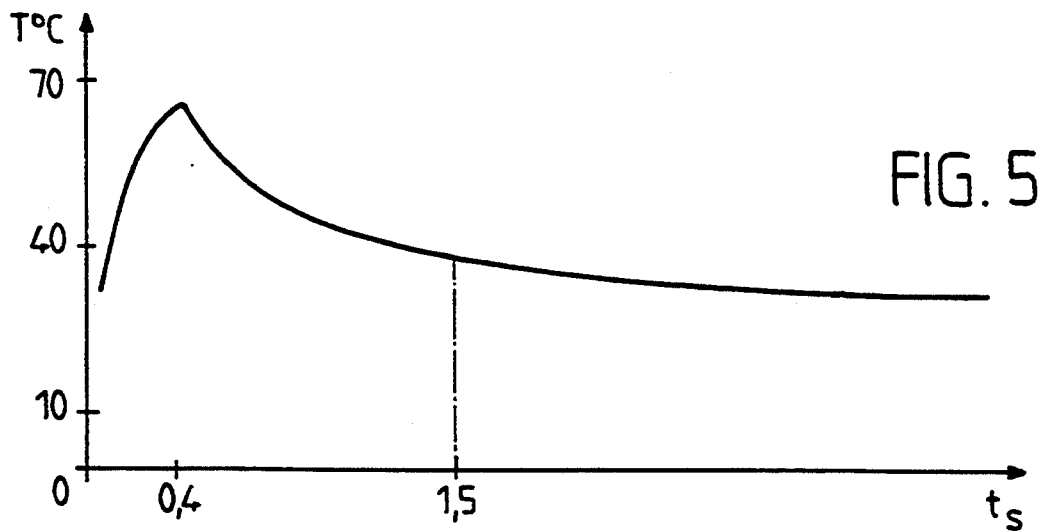
FIG. 5 shows the variations in temperature of a point A, in FIG. 4, after a shot, as a function of time.
Figure 4:
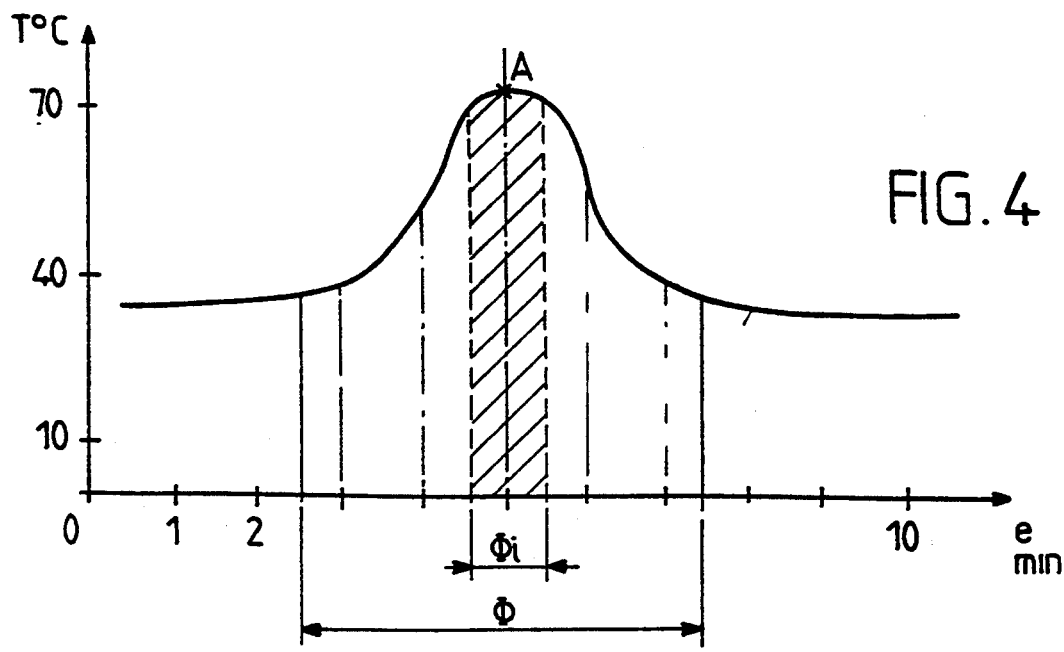
FIG. 4 shows the variations in temperature, at the cross section IV—IV of FIG. 3, as a function of distance in relation to the shot.

It is then important to observe the two parameters that have been previously defined, the relaxation time as illustrated in FIG. 4 and the Φ diameter area of temperature diffusion, as shown in FIG. 5.

Figure 11:
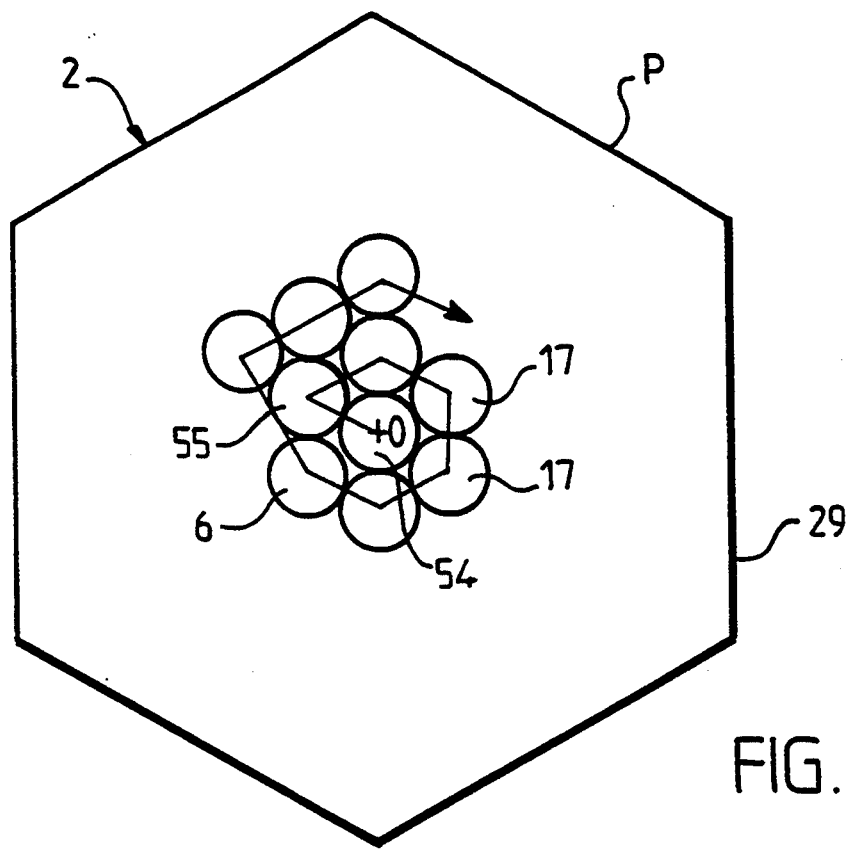
FIG. 11 illustrates a first scanning mode acting on the optical fiber of the treatment instrument of the present invention permitting a sequence of consecutive, contiguous impacts.
Figure 12:
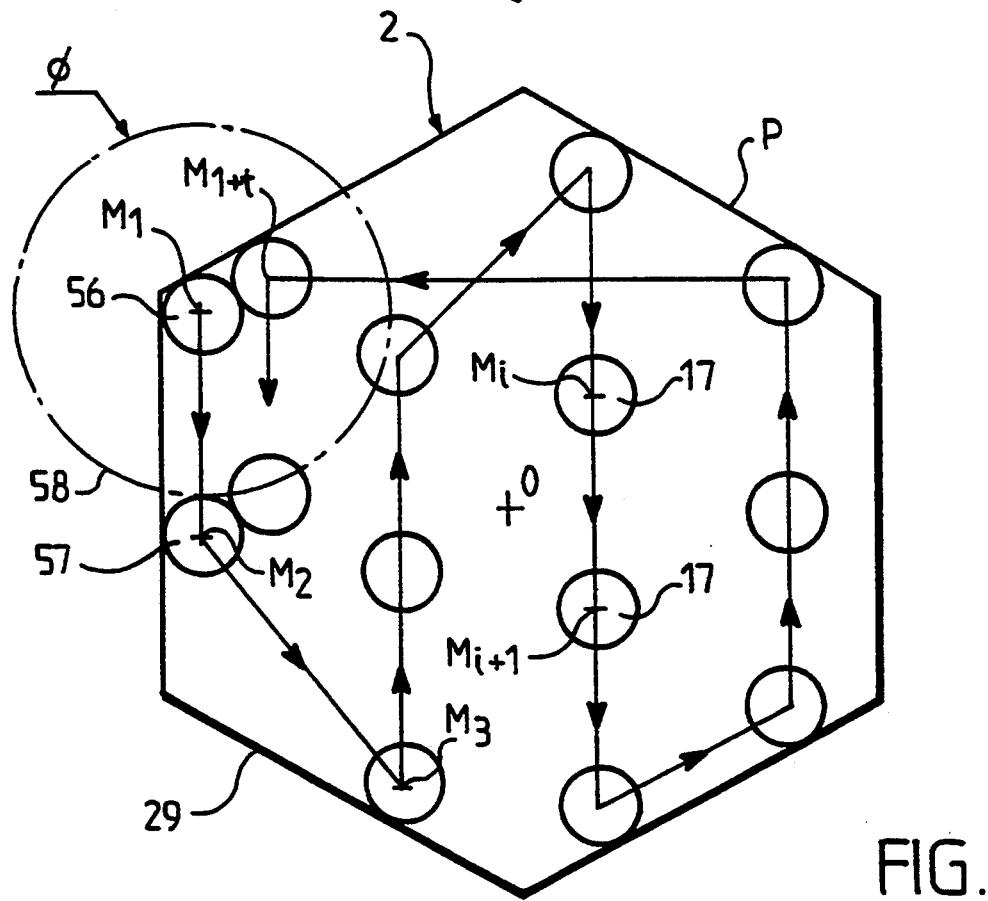
FIG. 12 represents another preferred scanning mode and illustrates a sequence of consecutive laser shots forming resulting, non-contiguous impacts, the impacts being all juxtaposed, however, by the end of the sequence, to cover the total surface area as shown, in particular, in FIG. 7.

This being the case, at least two optimized sequences of shots, such as those illustrated in FIGS. 11 or 12, for example, can be contemplated, respectively optimum to avoid heat overdosage, or optimum to avoid heat overdosage and have a minimum treatment time.

The elementary surface takes the form, in particular, of a geometrical figure having a centre "o" and a perimeter "P".

It should be noted in this connection that good results have been obtained by choosing an elementary surface in the form of a regular hexagon the diagonal of which can be adjusted between 3 and 20 mm. Such a choice makes it easier subsequently for the practitioner to distribute manually the elementary surfaces 2 of adjoining hexagons, their mutual joining being perfect along six different sides at 60°. In addition, a hexagon is the geometrical continuation of a basic triangle formed by three mutually contiguous circular impacts 17.

In the first scanning mode, as illustrated in FIG. 11, the following steps are performed:

the first shot is made and the first resulting impact 54 is produced substantially at the centre "o" of elementary surface 2, the second end 9 of the optical fiber 5 is positioned so that the second consecutive impact 55 is juxtaposed to the said first impact 54, and so on, continuing on around the first impact 54 along a spiral path towards the perimeter "P", as especially illustrated in FIG. 11, the second and following shots are made observing a period of delay between each consecutive shot equal to or greater than the given thermal relaxation time, for example with a delay time greater than or equal to 1.5 seconds.

In this case, the treatment time is relatively long as it corresponds to the firing time plus 1.5 times the number of impacts produced.

That is why, according to the present invention, the inventors have devised another, optimized, scanning mode permitting a firing interval between two consecutive shots of well under one second. This scanning mode is illustrated, for example, in FIG. 12. In this case:

the first shot is made at a point $M_1$ and the first impact 56 is produced inside the perimeter "P", for example in an angle of the hexagon, the said second end 9 of the optical fiber 5 is positioned so that the second consecutive impact 57 is produced, at a point $M_2$, inside the perimeter "P", but outside the given diameter area 58 of temperature diffusion around the first impact 56, the second and following shots are made, each time observing a firing distance $M_1M_2, M_2M_3, \ldots M_iM_{i+1}\ldots$ between each shot such that $M_1M_2 \ldots M_iM_{i+1}$ is greater than or equal to of area 58, in this case with a time lapse between each shot that can be less than the relaxation time, finally, the juxtaposition of two impacts $M_1M_{1+t}\ldots M_iM_{i+t}$ is permitted, in the firing sequence, when the delay time between the said impacts $M_i$ and $M_{i+t}$ is greater than or equal to the given thermal relaxation time.

Good results have been obtained by allowing for a relaxation time of at least 1.5 seconds and a diffusion area diameter of at least 5 mm for an impact 17 of one millimeter. Furthermore, such a scanning mode makes it possible to dispense with the local anaethesia.

Furthermore, the time lapse between each shot can be limited, in particular, to the mechanical response time of the sequential scanning means for displacing the end of the optical fiber, for example on the order of 140 milliseconds. The laser firing sequence then permits, in this case, at least eleven so-called non-contiguous shots between two contiguous impacts $M_iM_{i+t}$.

Such treatment processes according to the present invention can be implemented through the use of automatic control means with memory, 42, for controlling in time and space the sequential scanning of the second end 9 of optical fiber 5, these means permitting a sequence of consecutive laser shots such that:

on one hand, two consecutive laser shots 54,55;56,57 form two resulting impacts that are not contiguous, either on the abscissa or on the ordinate, if the time lapse between the two consecutive laser shots is less than the given thermal relaxation time, on the other hand, the impacts of the different consecutive laser shots completely cover the elementary surface through contiguous juxtaposition of the different impacts 17 resulting from the different laser shots, this being at the end of the sequence, as illustrated specifically in FIG. 7.

Figure 6:
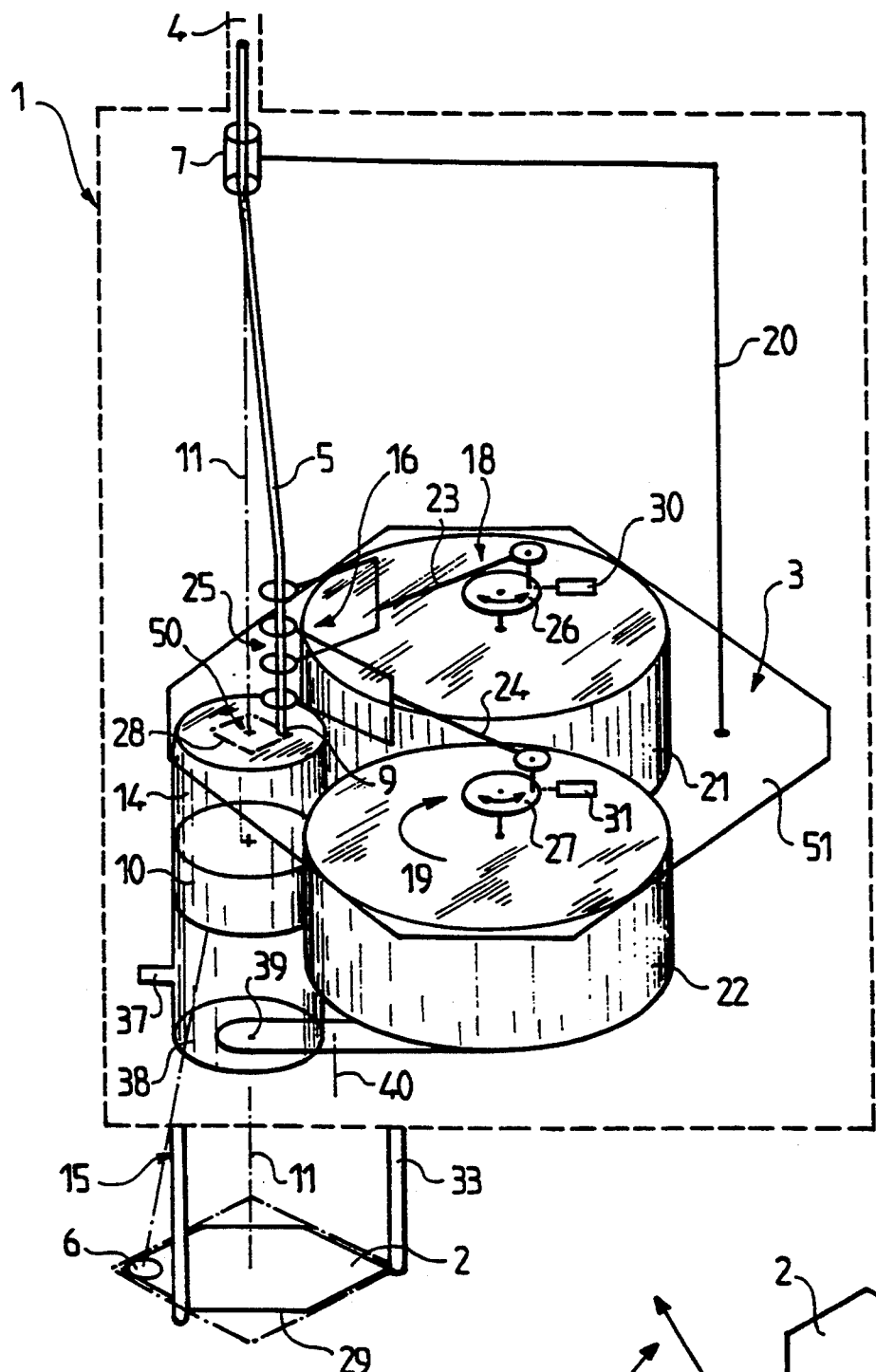
FIG. 6 represents a diagrammatic perspective view of a form of embodiment of the treatment apparatus of the present invention serving to illustrate its operating principle.
Figure 9:
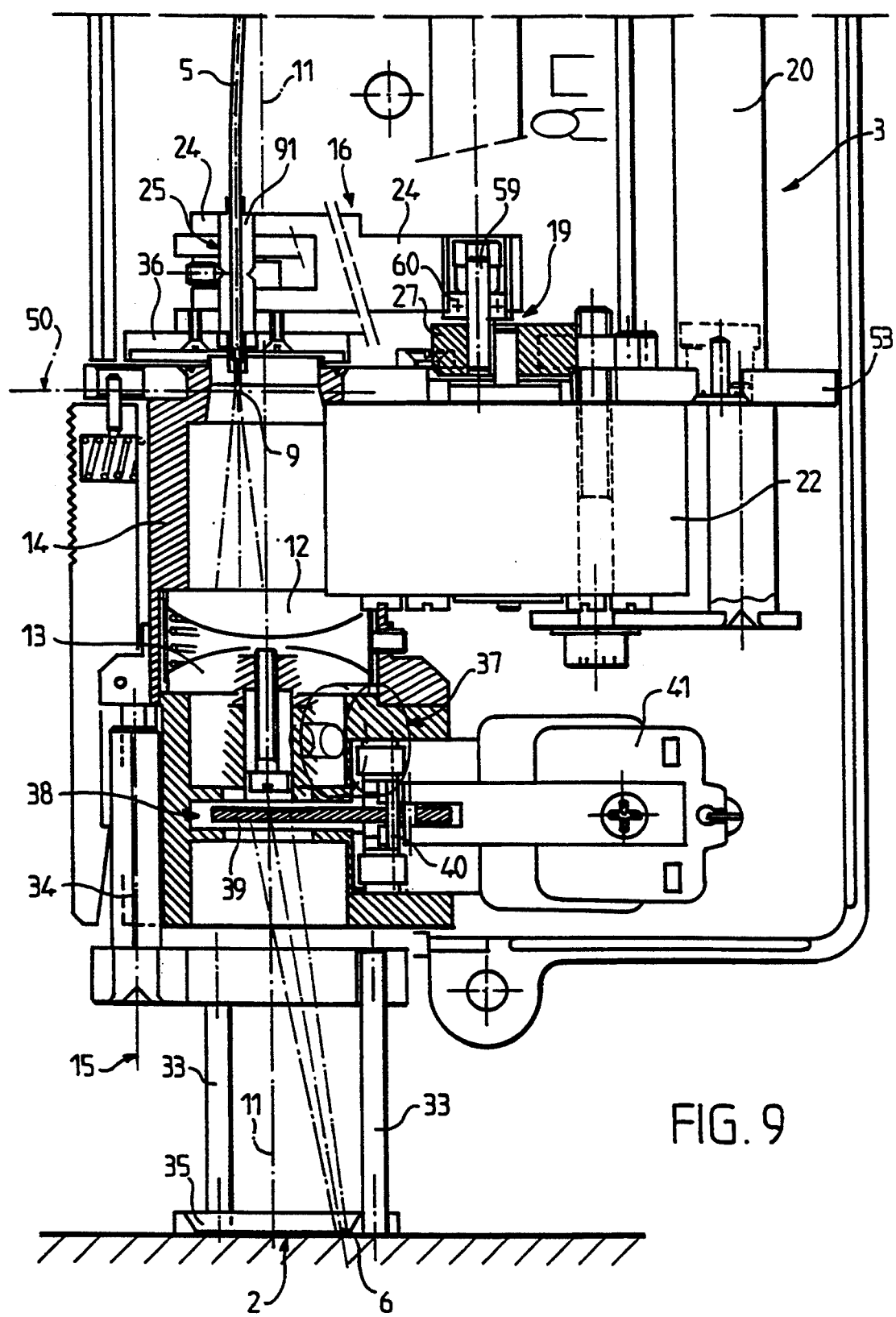
FIG. 9 shows an enlarged partial view of the lower portion of the instrument represented in FIG. 8.

This being the case, as shown in the preferred embodiment of FIGS. 6, 8 and 9, the sequential scanning means 16 are constituted by a mechanical device sequentially displacing the end 9 of optical fiber 5 in a plane 50 perpendicular to the main optical axis 11 in order to obtain the displacement and referenced positioning of displaceable spot 6 over the entire elementary surface 2 under investigation, in particular via the aforementioned imaging lens system 10. Thus, a series of laser shots can be effected sequentially in order to cover the entire elementary surface 2 under investigation.

The mechanical device producing this bi-axial movement is formed in particular by two connecting rod-crankshaft systems 18 and 19, both integral with frame 3 and mounted on plate 53; there is thus formed a system that is fixed in relation to frame 3, the fixed point 7 of the optical fiber and connecting rod-crankshaft systems 18 and 19 being joined via a bracket 20.

As shown more specifically in FIG. 9, the two connecting rod-crankshaft systems 18 and 19 are each driven by a motor, 21 and 22 respectively, cooperating with each other at the ends of each connecting rod, numbered 23 and 24 respectively, to form a common articulation 25 to which is secured end 9 of optical fiber 5.

In order to displace optical fiber 5 on the abscissa and the ordinate referenced in plane 50 by forming an area susbtantially similar to the area under investigation 2, the motor means, 21,22 of each connecting rod-crankshaft system, 18,19, are controlled independently and their rotation is controlled to produce sequential scanning by free end 9 of the optical fiber of the entire surface area corresponding to the elementary area of treatment 2.

Thus, if the angles of rotation are established for the crankshafts respectively numbered 26 and 27, movement and relative positioning are obtained for articulation 25 in relation to main optical axis 11. In addition, if their relative and absolute angular velocities are established, the path of the movement and its speed are also defined, The path of movement thus takes on the shape of a pseudo-lozenge 28, as can be seen from FIG. 6, the sides of which are parts of a circle. It should be noted that, in this shape, it is possible to inscribe, for instance, a hexagon 29 formed by all of the positions actually used.

This system will be designed in such a way that the optical requirements are met and, in particular, care will be taken to ensure that one portion of end 9 of optical fiber 5 is substantially parallel to optical axis 11; this can be achieved advantageously by dividing articulation 25 into two, as shown in FIGS. 6, 8 and 9. In addition, care will be taken to ensure that the optical fiber is not exposed to undue bending, so as to avoid mechanical fatigue as well as optical losses.

In this connection, it should be noted that the fiber will thus undergo inverted double bending, in one case from its fixed point 7 and, in the other case, from the axis of articulation 25, which results in axial shortening of the fiber.

Optical fiber manufacturers indicate certain mechanical and optical characteristics of their fibers making it possible to work without setting up stress or causing any optical loss.

In particular, these characteristics include the maximum stresses induced when the fiber is subjected to bending, and the fiber and its mounting will thus be determined in the light of these values.

Good results have been obtained notably when using a fiber having a core diameter of 400 microns, with maximum fiber eccentricity in relation to horizontal optical axis 11 of 2.5 mm, and a length between the two fixing points, 7 and 25, of 50 mm, the fiber then presenting a double curvature the radius of which is not less than 250 mm, that is to say twice the minimum recommended by the manufacturers.

Such bending is perfectly compatible with the limits laid down for correct operation, both mechanical and optical.

It should be borne in mind that the means and methods of assembling optical fibers, in particular to their connectors, whether it be by bonding or crimping, are known to one skilled in the art. Here, for example, use is made of elastic crimping by a stuffing box at fixed points 7,8,90. As to articulation 25, end 9 of the fiber is bonded in sleeve 91, in accordance with the conventional techniques, then this sleeve is immobilized in the aforementioned double articulation of connecting rods 23,24.

In this way, fatigue stresss and optical losses due to double bending, as well as the optical consequences of shortening, can be disregarded if the length of the fiber subjected to stress between these two fixing points 7 and 25 is sufficient.

In this connection, as to the crankshaft pins 59, the connecting rod bearings are designed on the basis of a single row ball bearing 60. Such an arrangement thus allows certain degrees of spherical freedom to be retained.

It is through its mechanical properties, hence through the elastic suspension by bending lines thus created, that the fiber and its shouldered sleeve 91 stabilize these degrees of freedom. Conversely, it is also these degrees of spherical freedom that absorb the axial movement of articulation 25, which is on the order of 75 microns in the case of the aforementioned dimensions, caused by the difference in axial length of the fiber in central position and its length shortened by its double bending in off-centered position.

In other words, the fiber is not, therefore, exposed to any stress other than bending, the values for the latter being nonetheless calculated so as to be well within the security limits in order to avoid impairing wave transmission qualities. Finally, with regard to the different optical aberrations, such as wave front, losses, which could be ascribable to double bending, these are negligible, according to the fiber manufacturers, starting from the "equilibrium length", that is to say more precisely that they are linked only to the number of random curvatures encountered all along the fiber that could mix the modes sufficiently, and stabilize variations in loss; the two additional end bending stresses applied thus become negligible. Furthermore, even if there remained variations in Gaussian curvature, the optical imaging means would overcome this problem.

The sequential scanning means thus obtained therefore form an isostatic structure in which the optical fiber plays the part of a mobile assembly in relation to frame 3.

As to the actual drive means for the connecting rod-crankshaft systems, 18,19, the motor means 21 and 22 take the form of "stepping" motors supplied by predetermined analog current levels enabling the "standard steps" of the motors to be divided into several "microsteps" in order to increase positioning accuracy.

To take a non-limitative example, the main steps are divided linearly into 32 micro-steps giving a positioning resolution of 0,02 mm with reference to the 1 mm displaceable spots, which will permit amply sufficient resolution when applying the treatment under consideration.

On the other hand, as the angular rotation of each motor, 21,22 is relative, absolute initialization sequences are needed for controlling their positioning. In this respect, each connecting rod-crankshaft system 18,19 is servoed to a position sensor, numbered 30,31 respectively, permitting periodic initialization of the positioning of motor elements 21,22.

As to the practical embodiment of this initialization device, the sensors used will be opto-electronic position sensors fixed in relation to the frame 3 and positioned opposite an index placed on crankshafts 26,27. In addition, it should be noted that this set of sensors does not require any particular accuracy as it identifies only positions corresponding to each repeated sequence, for example every four steps as, in this case, an identical electrical condition is found for the motor.

It should be noted that, in this way, it is possible to avoid the use of continuous servo control sensors such as potentiometer sensors or optical coders, which are more difficult to use and more expensive.

On the other hand, the mechanical angular adjustment of motors 21,22 has to be perfect. This is achieved by clamping them, as at 32, to plate 53 to immobilize them with respect to the frame 3, using known techniques.

As regards the positioning means 15 of the assembly formed, on one hand, by end 9 of optical fiber 5 and, on the other hand, by the imaging means 10, these position the assembly relatively with respect to the area of the body under investigation 2. They are constituted, as shown by FIGS. 6, 8 and 9, by a group of distance pieces 33, fixed beneath the frame 3 and centered on the main optical axis 11. These means serve to rest the apparatus on body area 2 and the firing distance, hence the desired size and uniformity, can thus be fixed.

For example, this positioning assembly is composed of three parallel columns arranged at 120°, forming a tripod centered on optical axis 11. In addition, the center to center distances of the columns correspond to the distribution intervals of a hexagon, forming the elementary surface aforementioned. These columns support a window 35, cut out according to the same hexagon.

In addition, this group of distance pieces 33 will be provided with adjustment means 34 for adapting the firing distance to the desired value, at the time of construction, as a function of manufacture. A mechanical construction of this type is within reach of one skilled in the art.

Figures 2A, 2B, 2C:
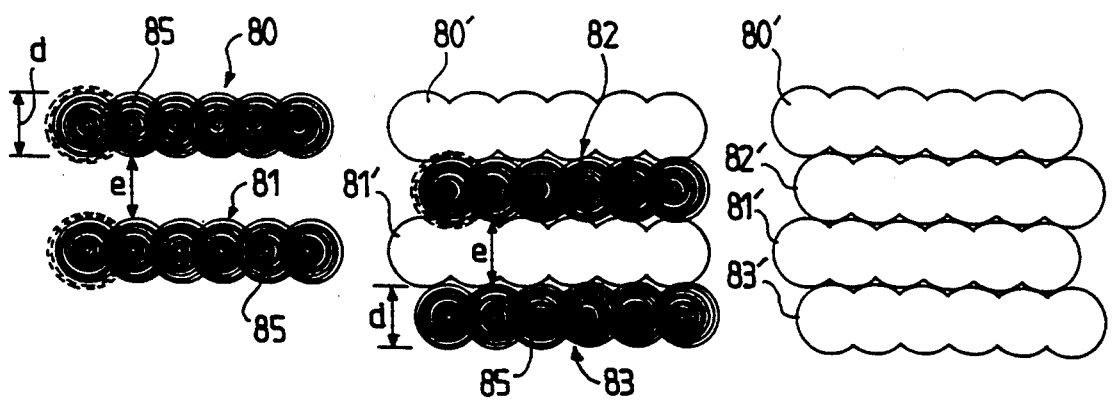
FIGS. 2a to 2c illustrate a known process for the treatment of skin angiomas, generally known as the "zebrine pattern".

Furthermore, to facilitate positioning, by the practitioner, of the different elementary surfaces corresponding to the areas under investigation 2, as shown in FIG. 2, there can be provided an independent adhesive support, not shown, previously applied to the patient's epidermis, this support comprising visible positioning marks consistent with the geometrical shape of elementary surface 2. The group of distance pieces 33 will then advantageously have a cut out window, at dermis level, which will facilitate its positioning with respect to the adhesive support.

Furthermore, according to the present invention, the irradiation power of the laser source is controlled and, in this respect, treatment instrument 1 is provided with means for measuring the power of the laser radiation emitted.

These measuring means are based on the integrating sphere principle, which provides a reliable method of indirectly measuring total radiated power.

In this connection, one skilled in the art is familiar with the principle of light measurement using such an integrating sphere in order to determine the total radiated power by an indirect measurement method. U.S. Pat. No. 4,580,557, for example, shows such an integrating sphere.

The principle of this measuring apparatus involves the use of a completely closed light trap which mixes the radiation and makes it uniform, For this purpose, the light source is placed inside the sphere.

To measure light, in the case of known integrating spheres, a measuring sensor is placed inside the sphere, but not opposite the source or opposite a major point of reflection.

According to the present invention, a "pseudo-integrating sphere" is formed, that is to say the principle of the known integrating sphere is applied, but there is no sphere structurally speaking.

In the case of the invention, the light source is formed by the end of the optical fiber and the pseudo-integrating sphere is constituted by mounting 14 supporting the imaging lens system 10.

A substantially cylindrical enclosed space is thus formed by means of the mounting 14, the movable cover 36 and the shutter 38,39. The situation is thus as follows: end 9 of optical fiber 5 is located in an enclosed space that is designed in such a way that all of these surfaces reflect and diffuse the specific laser radiation.

Then, part of this radiation is sampled via a photoelectric sensor 37, particularly shown in dotted lines in FIG. 9, which, depending on prior calibration, will enable the light present at this level to be controlled and detected.

Part of the total radiation diffused is sampled and measured by the detector 37, which will advantageously be provided with a filter appropriate to the laser. In addition, optical fiber 5 will be positioned during measurement coaxially with the main optical axis 11, and the measurement properly speaking will be carried out and processed using techniques that are within the competence of one skilled in the art.

Finally as to the optical portion proper of the handheld instrument of the present invention, this includes shutter means 38 which are controlled and synchronized with the scanning means 16 to control the exposure time of each shot independently of the operating conditions of the laser source.

More precisely, shutter 38 is constituted by a vane 39 that is movable angularly about an axis 40 parallel with the main optical axis 11. It is driven by a mechanical system of the lever arm type, driven in turn by an electromagnet 41, for example. Such a construction is also well known to one skilled in the art.

However, the shutter plane has been selected to lie in a privileged, non-focal area formed by the pseudo-focus of the beams generated by the diaphragm nature of the object source. In addition, the vane is made of a reflecting and diffusing material such as aluminium alloy.

Moreover, to direct the automatic operation of the different means described above, instrument 1 of the present invention comprises an automatic control unit associated with the instrument and organized about an electronic central unit, a time base and ancillary circuits which further permit control of the scanning means, measurement of irradiation power, control over the synchronized shutter means and dialogue with the operator.

In addition, if the power of laser radiation emitted, exposure time and the surface area of the spot generated are known, the central unit will enable fluence to be determined.

These different electronic elements will consist of electronic components such as microprocessors, random access memories, read only memories and other integrated circuits, the use of which is within the competence of one skilled in the art in question.

However, as regards the control circuit for the scanning means, it comprises at least one memory into which data is entered in order to permit a sequence of laser shots to cover with their impact 17 a geometrical FIG. 29 by juxtaposition of the impacts, perfectly reproducible in time.

Figure 10:
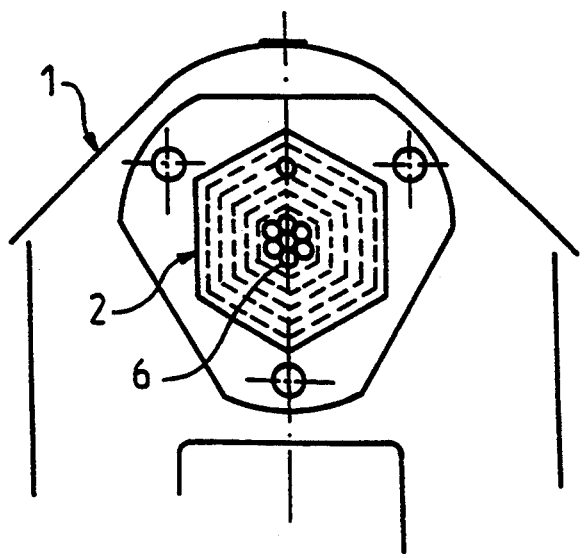
FIG. 10 shows a partial schematic bottom view of the instrument represented in FIGS. 8 and 9, which shows the modularity of the elementary surface treated.

In addition, the control electronics are designed in such a way that it is possible, via the dialogue circuit and the control circuit for the scanning means, to modulate the surface of the geometrical Figure, as shown, in particular, in FIG. 10. In this respect, it is possible to permit, for example, a choice of six equally distributed positions, permitting, in particular, hexagons with diagonals of between 3 and 20 mm, each position being centered on the main axis 11.

As specified hereabove, one of the original aspects of the present invention relates to the order in which the laser shots are automatically distributed in order to cover completely, by the end of a sequence of shots, the elementary surface of the area under investigation 2 by contiguously juxtaposing the different impacts 17 induced during the sequence.

However, it should be borne in mind that, during cinethermography of an isolated laser shot raising the temperature at the impact from 60° to 80° C., there was recorded a thermal relaxation time in the order of 1.5 seconds after this shot with temperature diffusion confined to a diameter of 3 to 4 mm at the level of the dermis.

Thus, repeated, juxtaposed shots, in this area of diffusion and before thermal relaxation, bring about a phenomenon of accumulation and, consequently, a temperature overload.

This phenomenon is negligible in the case of a manual technique such as currently applied by a practitioner, since the positioning times are far longer than the thermal relaxation times. On the other hand, during very fast automatic scanning, repeated juxtaposed shots necessitate a time delay between each shot so that thermal relaxation can take place.

This thermal accumulation phenomenon adversely affects the time needed to treat a given area, which is why the present invention proposes an optimized scanning mode as described above in order to cover the elementary surface under investigation in a cycle time of less than one minute and even approximating 40 seconds.

This scanning mode permitted by the sequential scanning means of the present invention enables at least two consecutive laser shots to be made without the resulting impacts 17 being thereby contiguous, the object of this being to avoid the effects of thermal accumulation due to temperature diffusion at the periphery of an impact. Nonetheless, upon completion of this sequence, all impacts 17 will be juxtaposed and perfectly contiguous with one another.

Reference should be made in this connection to FIG. 12 which, it should be borne in mind, shows an optimized sequential scanning order whereby impacts 17, 56, 57 have a diameter substantially approximating one millimeter, an interval of at least two millimeters then being observed between each shot $M_iM_{i+1}$ to avoid accumulation phenomena.

In this case, the automatic control unit of the system and its scanning means control circuit are programmed by software that permits loctaion on the abscissa and the ordinate of the different positions of displaceable spot 6 and displacement of the optical fiber in this respect by controlled rotations of the drive means, 21 and 22, of scanning system 16. The scanning mode illustrated is completely arbitrary and other scanning modes obtained by different programming could be contemplated.

However, it should be noted that the control unit comprises means for disabling the sequential scanning of laser shots in order to permit fixed positioning for traditional manual usage, for example for retouching purposes.

Figure 13:
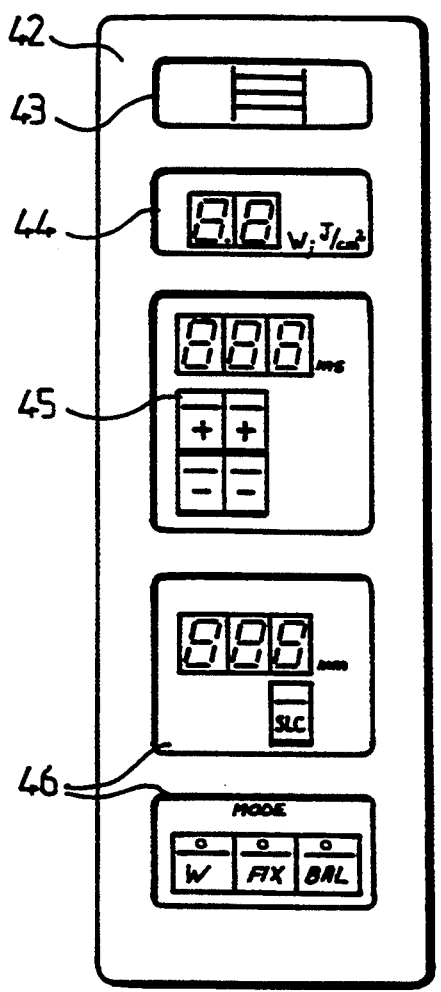
FIG. 13 shows a detailed external view of the treatment instrument of the present invention which illustrates the display means and means of interaction with the operator.

Furthermore, to introduce the different data and initiate the desired mode of use, the practitioner has at his disposal a display and control panel 42, as represented in FIG. 13, which is advantageously separate from treatment, instrument 1 proper in order to keep overall dimensions within reasonable limits. The same applies, moreover, to the location of the aforementioned control unit.

The control panel 42 will make it possible, for example, to dispose of test lamps, as at 43, to monitor the internal operation of the system, to read the power and/or fluence measurement via a display, as at 44, to control the exposure time and enter the corresponding data, as at 45, to select the scanning type and to choose the size of the treatment area, as at 46. These different elements are designed using current electronic technologies.

Finally, to facilitate the practitioner's task in the treatment, treatment instrument 1 of the present invention can be advantageously supported by the arm 48 of a bracket 47, the electronic central unit and the control panel 42 being disposed on the upright of bracket 47, particularly as at 49 in FIG. 14.

It goes without saying that other embodiments of the present invention, within the competence of one skilled in the art, could be contemplated without thereby departing from the scope thereof.

We claim:

1. An apparatus for treating a region of tissue with a laser beam comprising:
   a handpiece, said handpiece including a means for supporting the handpiece at a fixed position on the tissue within the region to be treated;
   means for coupling the beam into the handpiece;
   guide means located within said handpiece for directing the beam to a spot on the tissue within the region to be treated;
   adjustment means coupled to said guide means for varying the position of the spot within the region to be treated while the handpiece remains at a fixed position on the tissue; and
   processor means for controlling the adjustment means to direct the spot to a series of nonoverlapping continuous positions covering the region to be treated, said processor means further controlling the beam to irradiate each position of the spot with an output, with the output at each spot having a predetermined duration and power and power wherein the tissue is not irradiated during the time the adjustment means varies the position of the spot and with the positions being selected so that if the time period between the delivery of the beam at two different positions is less than the thermal relaxation time of the tissue, then the distance between those two positions will be greater than the thermal diffusion distance thereby avoiding overheating of the tissue while minimizing the time period necessary for treating the entire region.

2. An apparatus as recited in claim 1 wherein said region to be treated has a hexagon configuration.

3. An apparatus as recited in claim 1 wherein said guide means includes an optical fiber having an input end and a delivery end and wherein said adjustment means functions to translate the position of the delivery end of the fiber.

4. An apparatus as recited in claim 3 wherein said guide means further includes a lens optically aligned with the delivery end of the fiber and wherein the position of the delivery end of the fiber is translated in a plane parallel to plane of the lens and relative to the optical axis of the lens thereby adjusting the position of the spot on the tissue.

5. An apparatus as recited in claim 4 further including a shutter means controlled by said processor means and functioning to control the duration which the treatment beam is delivered at each position of the spot.

6. An apparatus as recited in claim 5 further including a means for measuring the power of the treatment beam delivered by said optical fiber and generating a control signal which is monitored by said processor means.

7. An apparatus as recited in claim 3 wherein said handpiece is configured so that the delivery end of said fiber is spaced from the tissue to be treated.

8. A method of treating a region of tissue with a treatment beam from a laser source comprising the steps of:
   a) selecting a first spot within the region to be treated;
   b) irradiating the first spot with the beam for a predetermined time and at a predetermined energy;
   c) selecting a second spot within the region to be treated during which time the tissue is not being irradiated;
   d) irradiating said second spot with the beam for a predetermined time and at a predetermined energy, with said first spot not overlapping said second spot and wherein the position of the second spot is selected so that if the time period between the delivery of the beam at the first and second spots is less than the thermal relaxation time of the tissue, then the distance between those two spots will be greater than the thermal diffusion distance; and
   e) repeating steps (c) and (d) to irradiate additional nonoverlapping spots until the entire region has been treated with a pattern of contiguous spots such that overheating of the tissue is minimized while reducing the time period necessary for treating the entire region.

* * * * *